United States Patent
Plank et al.

(10) Patent No.: US 6,866,506 B2
(45) Date of Patent: Mar. 15, 2005

(54) LIGHT HARDENING APPARATUS PARTICULARLY FOR A DENTAL PRACTICE

(75) Inventors: Wolfgang Plank, Rankweil (AT); Peter Burtscher, Rankweil (AT); Gottfried Rohner, Altstatten (CH)

(73) Assignee: Ivoclar Vivadent AG, Sohaan (LI)

( * ) Notice: Subject to any disclaimer, the term of this patent is extended or adjusted under 35 U.S.C. 154(b) by 136 days.

(21) Appl. No.: 10/139,307

(22) Filed: May 6, 2002

(65) Prior Publication Data

US 2002/0177098 A1 Nov. 28, 2002

Related U.S. Application Data

(60) Provisional application No. 60/305,236, filed on Jul. 13, 2001.

(30) Foreign Application Priority Data

May 23, 2001 (DE) .......................... 101 25 340

(51) Int. Cl.[7] .................................................. A61C 3/00
(52) U.S. Cl. .......................................................... 433/29
(58) Field of Search ........................... 433/29; 362/573; 250/504 R

(56) References Cited

U.S. PATENT DOCUMENTS

| | | | | |
|---|---|---|---|---|
| 5,420,768 A | * | 5/1995 | Kennedy | 362/119 |
| 5,634,711 A | * | 6/1997 | Kennedy et al. | 362/119 |
| 5,738,678 A | * | 4/1998 | Patel | 606/10 |
| 6,102,696 A | * | 8/2000 | Osterwalder et al. | 433/29 |
| 6,325,623 B1 | * | 12/2001 | Melnyk et al. | 433/29 |
| 6,331,111 B1 | * | 12/2001 | Cao | 433/29 |
| 6,695,614 B2 | * | 2/2004 | Plank | 433/29 |

FOREIGN PATENT DOCUMENTS

DE       295 11 927 U1      2/1997

* cited by examiner

Primary Examiner—John J Wilson
(74) Attorney, Agent, or Firm—John C. Thompson; Alan S. Korman

(57) ABSTRACT

A light hardening apparatus particularly suitable for effecting the hardening of dental restoration material is provided and includes two semiconductor light sources cooperable with a light-guiding element for guiding the light from the semiconductor light source to the dental restoration material to effect the hardening thereof. The two semiconductor light sources have an emission spectrum with at least two maximums of which one of the maximums lies at approximately 420 nm and the other maximum lies at approximately 470 nm.

13 Claims, 3 Drawing Sheets

LIGHT HARDENING APPARATUS PARTICULARLY FOR A DENTAL PRACTICE

CROSS REFERENCE TO RELATED APPLICATIONS

This application claims foreign priority benefits under 35 U.S.C. §119(a)–(d) from German patent application ser. no. 101 25 340.0 filed May 23, 2001. In addition, this application claims the benefit under 35 U.S.C. §119(e) of U.S. provisional patent application Ser. No. 60/305,236 filed Jul. 13, 2001.

BACKGROUND OF THE INVENTION

The present invention relates to a dental light hardening apparatus which is suitable not only for the complete hardening of photo polymerizable dental material but is also suitable for whitening of teeth as well as for deployment as a diagnostic apparatus for cavities. Other therapy possibilities, which are not herein mentioned, can be realized with the dental light hardening apparatus of the present invention. In the following description, the dental light hardening apparatus of the present invention is described including a configuration thereof as a dental restoration piece hardening apparatus.

Light devices have been deployed, among other applications, in dental applications in which a light polymerizable plastic is hardened by irradiation with light. In order to achieve a high light density, energy rich light sources are typically deployed such as halogen glow lamps, xenon photoflash, or even high-tension discharge lamps. The high-tension discharge lamps have, in fact, an especially high light intensity and, thereby, a correspondingly high light density. However, the operational tension reaches at least 3.5 kV and a corresponding activation device is required so that such lamps are not suitable for deployment in the dental practice-at least, insofar as hand operable devices are concerned.

Numerous attempts have been undertaken to improve the light density of the known light apparatus in order to achieve a complete hardening of the deeper lying layers in a rapid manner. A long-time known, conventional light hardening apparatus with a light intensity of, for example, 50 mW/cm$^2$ produces, in fact, by a correspondingly longer light irradiation, a good over surface hardening of the plastic or artificial piece that is to be polymerized. However, deeper lying layers are not at all hardened or, at most, only incompletely hardened. There arises a hardness gradient which leads to the result that the deeper lying, middle regions remain somewhat soft or that these regions are hardened completely at a time later than the complete hardening of the over surface areas.

The known light hardening apparatus lead to restoration results that are compromised by, or suffer from, in part, edge spalling problems. The known light hardenable plastics shrink slightly during the hardening process. With the known light hardening apparatus, a complete hardening initially occurs first in the over/outer regions of the restoration piece. The thereafter following complete hardening of the deeper lying, central regions leads to contractions and, thus, to edge spalling formation.

It is further known to deploy light hardening apparatus that work with semi-conductor light beam sources such as LEDs. For example, DE-GM 295 11 927 discloses a light-hardening device which uses a light diode which emits light in the blue spectral region which is supplied from a battery or an accumulator.

It has, additionally, already been proposed to deploy a plurality of LEDs for the energy supply of the light guiding conduit. In this manner, the light output of the light-hardening device is improved. Independent of whether the LEDs are configured as module—that is, in a common plastic housing—or as individual LEDs—that is, each respectively disposed in an individual plastic housing the light output of such arrangements is limited. The plastic surroundings do not effect an electrical insulation of the LEDs but, instead, block the transfer or giving off of heat by the LEDs, so that it is necessary, even with a cooling of the plastic housing from the exterior, that a predetermined density of the light emitting chips not be exceeded.

It has further been proposed to use a light emitting diode as a semi-conductor light source, which emits light in the visible or ultraviolet range. However, there are disadvantages associated with this approach. Investigations have shown that color changes occur precisely in connection with light or non-dark materials. On the other hand, such conventional systems do not permit the use of white photo initiators.

At the same time, the tendency of the dental restoration piece to suffer from edge spalling formation remains unabated in connection with the conventional systems.

OBJECTS AND SUMMARY OF THE INVENTION

The present invention offers a solution to the challenge of a light hardening apparatus for dental practice, which reduces the tendency of light-hardenable masses to incur edge-spalling formation while at the same time permitting fabrication of such light hardening apparatus in a cost favorable manner and offering a light hardening apparatus that is flexible in its deployment.

In accordance with the present invention, one embodiment of the light hardening apparatus includes a semi-conductor light source with an emission spectrum of at least two maximums. In accordance with the present invention, the two maximums are clearly separate from one another. For the first time, the possibility is offered to use plastic or artificial material which comprises two different catalyst systems which harden one after the other. In accordance with the present invention, the tendency towards edge spalling formation is reduced.

In accordance with the present invention, it is particularly advantageous that the light emitting source can be comprised of two different wavelengths for complete hardening of the material simultaneously, in order to effect the excitation of all dental materials initiators from 400 to 500 nm.

Through the excitation of a semiconductor light source with an emission spectrum, whose maximum corresponds to the spectral sensitivity of a first catalyzer, a pre-hardening is undertaken. As necessary, a follow-up working of the material can already have been accomplished in that the plastic or artificial material in this condition exhibits a high viscosity but is nonetheless malleable. By activation of the other lighting source with an emission spectrum having a maximum which is clearly different than the first maximum and is, preferably, of a short wavelength, the second catalyzer can be activated whose sensitivity maximum corresponds to the second maximum. Preferably, this sensitivity maximum lies around 420 nm. The plastic or artificial material can be brought to complete hardness by the activation of this catalyst.

Surprisingly, the solution of the present invention allows adjustment without further working or special measures to nonetheless yield a reduced tendency towards edge spalling formation. Through the heretofore conventional light hardening by means of a light source in connection with the deployment of a catalyzer, the hardening typically follows a course by which at first the thinner edge layers and the over surface layers of the dental restoration piece are hardened. Thereafter, the deeper lying and central layers of the dental materials, which light emissions, due to their penetration depth, have more difficulty in reaching, are hardened. By virtue of the contraction of these deeper lying and central layers, edge spalling is produced in that the over surface region and the edge region of the dental restoration piece typically already have a higher firmness or hardness than the still soft deeper lying middle region.

In contrast, in accordance with the present invention, the contraction by virtue of the hardening process occurs during a condition in which neither the material in the edge region nor the material in the middle region is yet completely hardened. In this manner, the adhesion forces clearly overcome the forces which resist malleability of the material so that the contraction or shrinking deformation occurs in such a manner that the layer strength of the material is somewhat reduced. This is not a problem and can, as necessary, also be handled by application of additional layers or can be compensated by a previously applied increased layer strength.

It is to be understood that as necessary and in connection with the operation of the apparatus, the possibility exists to select the catalyzer and the emission maximum with respect to one another and to accommodate these to a wide range of requirements. Thus, as necessary, a substantially long wavelength emission maximum can be realized for the first light source and the catalyzer for the first light source can have an emissions maximum of, for example, more than 500 nm. The dental material can be follow up treated with light as well as additional heat to effect the hardening thereof.

In accordance with the present invention, a dual hardening system is made possible.

In an advantageous embodiment of the light hardening apparatus of the present invention, the apparatus is deployed with the light sources directly on the teeth. In a particularly advantageous embodiment, a coupling sleeve (a pullover) is provided which can be disposed against the tooth in an elastic manner and which serves to deliver the emitted light completely onto the dental restoration piece. Due to this configuration, the hardening can be exactly reproduced in that the light output given off by the light hardening apparatus as well as the light output which ultimately reaches the dental restoration piece can be fixed in a predetermined manner.

Additional advantages, details, and features are provided in the hereinafter-following description of two embodiments of the light hardening apparatus of the present invention.

BRIEF DESCRIPTION OF THE DRAWINGS

The object and advantages of the present invention will appear more clearly from the following specification in conjunction with the accompanying drawings, in which.

DETAILED DESCRIPTION

Figure 1:
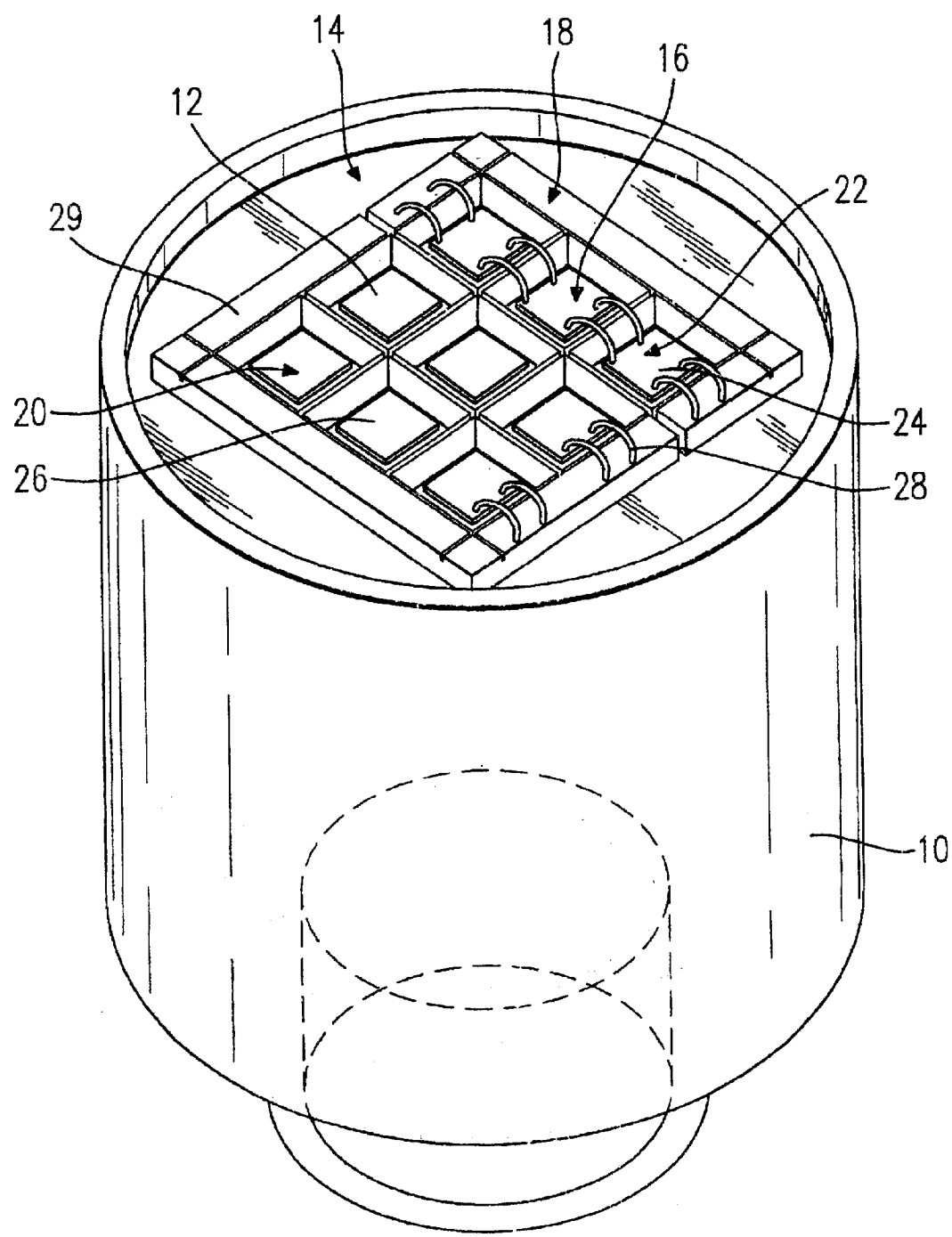
FIG. 1 is a perspective view of details of one embodiment of the light hardening device of the present invention for hardening a dental restoration piece and showing, in particular, a base body having integrated lighting sources thereon.

As seen in FIG. 1, a light hardening apparatus of the present invention suitable for complete hardening of dental restoration pieces includes a base body 10 having a plurality of LED-chips 12 on its upper side 14. The LED-chips 12 are each respectively disposed in a hollow or recess 16 and are in a sunken disposition with respect to the surface 18. In the one embodiment of the light hardening apparatus shown in FIG. 1, a total of nine of the LED-chips 12 are provided. By virtue of the sunken disposition of the LED-chips 12 in the recesses, there is produced a plurality of micro reflectors which increase the light output of the apparatus.

A portion of the LED-chips have an emission maximum of 470 nm. A further portion of the LED-chips have an emission maximum of 420 nm. Each of the portions is organized into a group of LED-chips which are commonly actuated, whereby the groups each have an output which is controlled by a dedicated control device operating independently of the control device for the other respective groups of LED-chips.

The LED-chips 12 of a first group 22 form the semiconductor light sources 24 having an emission maximum of 470 nm and the LED-chips 12 of a second group 20 form the semiconductor light sources 26 having an emission maximum of 420 nm.

Conventional bond wires 28 are arranged in an interconnecting manner over the individual LED-chips 12 of each group partially in a parallel actuation circuit, partially in a series actuation circuit, and are connected to collective rails 29.

The collective rails 29 are connected to separate energy supply connectors (not shown) and are connected with a control device (not shown).

Figure 2:
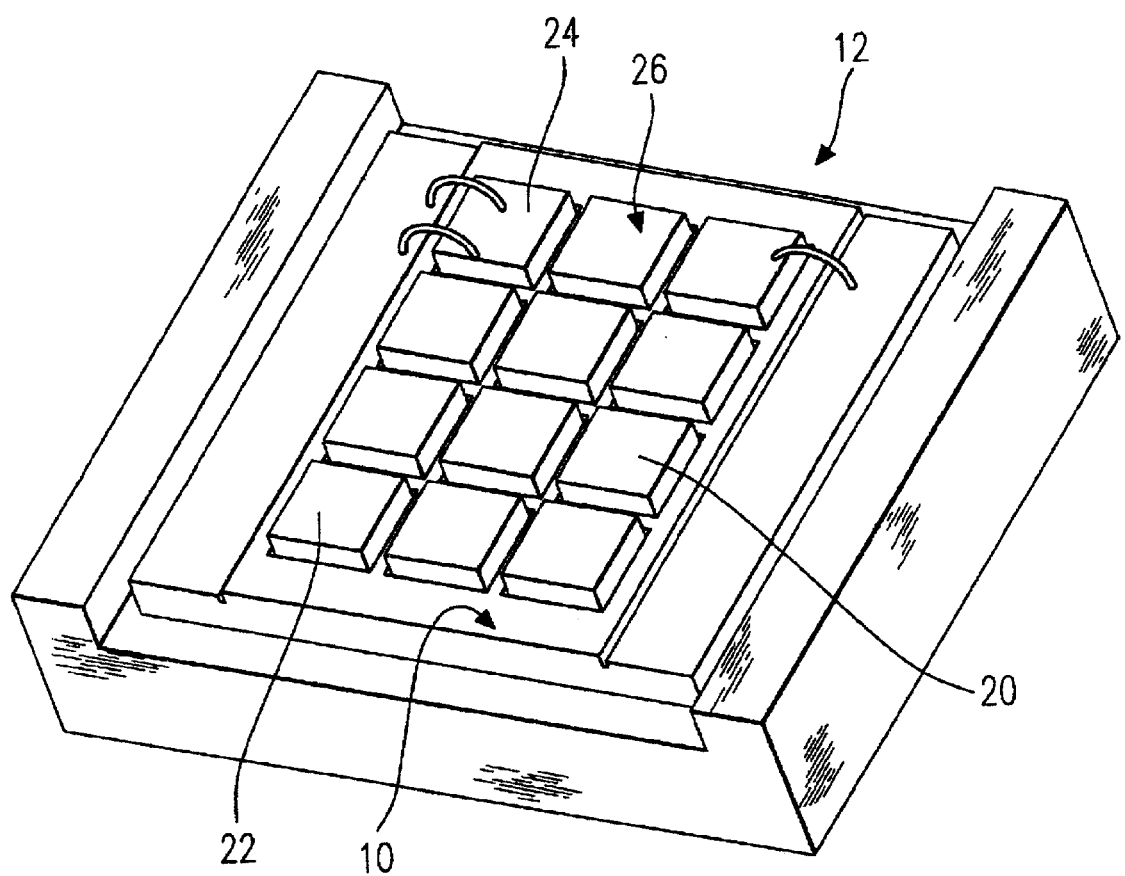
FIG. 2 is a perspective view of another embodiment of the light hardening apparatus of the present invention.

Another embodiment of the light hardening apparatus of the present invention is shown in FIG. 2. In this embodiment, the LED-chips 12 are mounted in close relationship with one another and here, as well, a first group of the LED-chips form the semiconductor light sources 24 and another group 20 of the LED-chips form the semiconductor light sources 26.

The control device associated with the first group 22 initially actuates the semiconductor light sources 24, whereby the light hardening apparatus, which is in immediate adjacent relationship with the over surface of the dental restoration piece, irradiates the dental restoration piece. In this condition, the first catalyzer is activated and this leads to a pre-hardening of the photo polymerizable mass. Thereafter, as desired, a follow up working is undertaken, if this is deemed to be necessary. Also, for example, an additional layer of dental restoration material can be applied.

Thereafter, the semiconductor light sources of the second group 20 are activated and a complete hardening is performed.

It is to be understood, that the light sources can be partitioned or distributed in any suitable desired manner within the scope of the present invention.

Figure 3:
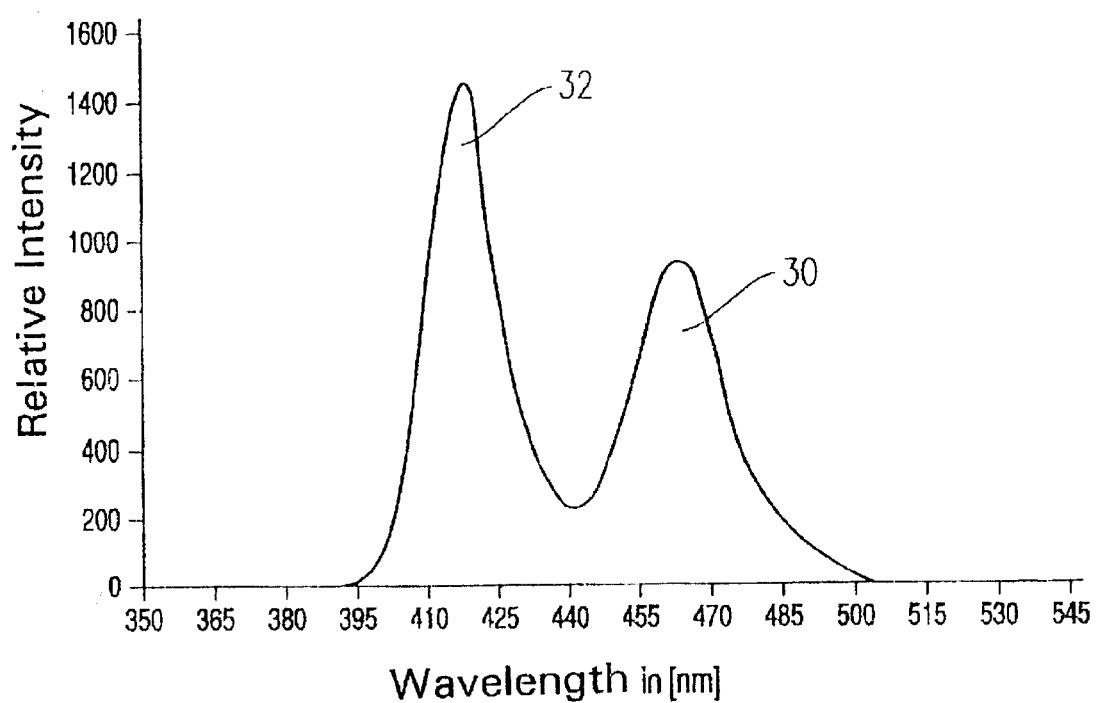
FIG. 3 is a graphical representation of a spectrum of the light sources of an embodiment of the light hardening apparatus of the present invention.

FIG. 3 graphically shows the emission of the light hardening apparatus of the present invention in the condition in which all of the semiconductor light sources have been activated. A first maximum 30 and a second maximum 32 can be seen, whereby the light intensity of the second maximum 32, which lies at approximately 420 nm, is clearly higher.

The present invention is, of course, in no way restricted to the specific disclosure of the specification and drawings, but also encompasses any modifications within the scope of the appended claims.

What is claimed is:

1. A light hardening apparatus for dental practice, comprising:
   a dental restoration material, wherein the dental restoration material includes photo initiators of differing types; and
   at least two semiconductor light sources cooperable with a light-guiding element for guiding the light from the semiconductor light sources to the dental restoration material to effect the hardening thereof, at least one semiconductor light source having an emission spectrum with a maximum which lies at approximately 420 nm, and wherein another of the at least two semiconductor light sources has an emission maximum which lies at approximately 470 nm.

2. A light hardening apparatus for dental practice according to claim 1, wherein the apparatus includes a third semiconductor light source having an emission maximum of at least 500 nm.

3. A light hardening apparatus for dental practice according to claim 1, further comprising a control device for controlling the semiconductor light sources independently of one another and being operable to control the semiconductor light sources with different emission maximums during differing time periods.

4. A light hardening apparatus for dental practice according to claim 3, wherein the control device is operable to activate the semiconductor light sources having an emission maximum of around 470 nm before the activation of another semiconductor light source having an emission maximum of approximately 420 nm.

5. A light hardening apparatus for dental practice according to claim 4 where the light in the long wavelength range of 470 nm will effect a pre-hardening of a dental restoration piece comprised of the dental restoration material, and the light in the short wavelength range of approximately 420 nm will effect a finish hardening of the dental restoration piece.

6. A light hardening apparatus according to claim 5, wherein the control device is operable to control the irradiation of the dental restoration piece such that the piece can be subjected to follow up work between the pre-hardening and finish hardening thereof.

7. A light hardening apparatus for dental practice according to claim 3, wherein the control device is operable to activate the semiconductor light source having an emission maximum of approximately 470 nm after the activation of a semiconductor light source having an emission maximum of approximately 420 nm.

8. A light hardening apparatus for dental practice according to claim 1, wherein the light intensity maximum includes a spectral spike of approximately 7 nm for a respective intensity increase or intensity decrease in correspondence with a factor of 3.

9. A light hardening apparatus for dental practice according to claim 1, whereby the relative light emission intensity between the maximums lies at a value of less than a ⅓ of the maximum light emission intensity.

10. A light hardening apparatus for dental practice according to claim 1, whereby the semiconductor light sources are configured with LED-chips which are disposed in relatively dense relationship with one another and which are disposable in the immediate proximity of a tooth for effecting complete hardening of the dental restoration material.

11. A light hardening apparatus for dental practice according to claim 1, whereby the semiconductor light sources are disposed at the head of the light hardening apparatus.

12. A light hardening apparatus for dental practice according to claim 1 and further comprising reflection areas extending around the light sources.

13. A light hardening apparatus according to claim 1, wherein the dental restoration material comprises two catalyzers, one of which has a spectral sensitivity maximum of approximately 420 nm.

* * * * *